(12) United States Patent
Narayanan

(10) Patent No.: US 6,677,119 B2
(45) Date of Patent: Jan. 13, 2004

(54) METHODS OF DETECTING A COLON CANCER CELL

(75) Inventor: Ramaswamy Narayanan, Delray Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 90 days.

(21) Appl. No.: 09/730,212

(22) Filed: Dec. 5, 2000

(65) Prior Publication Data

US 2002/0039727 A1 Apr. 4, 2002

Related U.S. Application Data

(60) Provisional application No. 60/200,292, filed on Apr. 28, 2000.

(51) Int. Cl.[7] .................. G01N 33/53; A61K 38/00; C07K 14/00; C07H 21/04
(52) U.S. Cl. .............. 435/6; 435/7.1; 435/7.9; 435/91.1; 530/300; 530/350; 530/387.1; 530/388.1; 530/389.1; 536/23.1; 536/23.5; 536/24.3; 536/24.31; 536/24.33
(58) Field of Search ................ 435/6, 7.1, 7.9, 435/91.1; 536/23.1, 23.5, 24.3, 24.31, 24.33; 530/300, 350, 387.1, 388.1, 389.1

(56) References Cited

U.S. PATENT DOCUMENTS

| | | | |
|---|---|---|---|
| 5,733,748 A | 3/1998 | Yu et al. | 435/70.1 |
| 5,861,494 A | 1/1999 | Soppet et al. | 536/23.1 |
| 5,922,855 A | 7/1999 | Liskay et al. | 536/23.5 |
| 6,080,722 A | 6/2000 | Soppet et al. | 514/12 |

FOREIGN PATENT DOCUMENTS

| | | | |
|---|---|---|---|
| WO | WO 98/58061 | | 12/1998 |
| WO | WO 99/55868 | | 11/1999 |
| WO | WO 00/04923 | | 2/2000 |
| WO | WO 00/38709 | | 7/2000 |
| WO | WO 00/55351 | * | 9/2000 |

OTHER PUBLICATIONS

A_Geneseq_101002, sequence search results #8–10 and 12–13.*
Sequence Alignment, result #1.*
Sequence Alignment, result #3.*
Budillon, A., "Molecular Genetics of Cancer," Cancer, 76: 1869, 1995.
Hunter, T., "Oncoprotein Networks," Cell, 88: 333, 1997.
Schwab, M., "Amplification of oncogenes in human cancer cells," BioEssays, 20: 473, 1998.
Golub et al., "Molecular Classification of Cancer: Class Discovery and Class Prediction by Gene Expression Monitoring," Science, 286: 531, 1999.
Zhang et al., "Gene Expression Profiles in Normal and Cancer Cells," Science, 276: 1268, 1997.
Latchman, D., "How can we use our growing understanding of gene transcription to discover effective new medicines?," Pharmaceutical biotechnology, 8: 713, 1997.
Berman, H., "The past and future of structure databases," Analytical Biotechnology, 10: 76, 1999.
Beck S. and P. Sterk, "Genome–scale DNA sequencing: where are we?," Analytical Biotechnology, 9: 116, 1998.
Huang, S., "Gene expression profiling, genetic networks, and cellular states: an integrating concept for tumorigenesis and drug discovery," J. Mol. Med., 77: 469, 1999.
Pollack, et al., "Genome–wide analysis of DNA copy–number changes using cDNA microarrays," Nature Genetics, 23: 41, 1999.
Schena et al., "Quantitative Monitoring of Gene Expression Patterns with a Complementary DNA Microarry," Science, 270: 467, 1995.
Rawlings, C. and D. Searls, "Computational gene discovery and human disease," Genetics of Disease, 7: 416, 1997.
Bains, W., "Company strategies for using bioinformatics," Tibtech, 14: 312, 1996.
Heller, R., "Discovery and analysis of inflammatory disease–related genes using cDNA microarrays," PNAS, 94: 2150, 1997.
Lal et al., "A Public Database for Gene Expression in Human Cancers," Cancer Research, 59: 5403, 1999.
Strausberg, et al., "New opportunities for uncovering the molecular basis of cancer," Nature Genetics special issue, 415, 1997.
Nacht, et al., "Combining Serial Analysis of Gene Expression and Array Technologies to Identify Genes Differentially Expressed in Breast Cancer," Cancer Research, 59: 5464, 1999.

* cited by examiner

*Primary Examiner*—Carla J. Myers
*Assistant Examiner*—Alexander H. Spiegler
(74) *Attorney, Agent, or Firm*—Akerman Senterfitt; Stanley Kim

(57) ABSTRACT

Nucleic acids and polypeptides correlated with cancer are disclosed. Also disclosed are methods of detecting cancer in a biological sample by determining expression of a colon carcinoma related gene (CCRG) or protein in that sample.

17 Claims, 7 Drawing Sheets

```
5'-  gcctcagaca gtggttcaaa gttttttctt cctttcagg tgtcgtgaaa agcttgaatt cggcgcgcca gatatcacac gtgccaaggg gctggctcaa ataaatctgt tcttcagcaa ccctacctgc ttctccaaaa ctgcctaaag agatccagta ctgatgacgc tgttcttcca tctttactcc ctggaaacta accacgttgt cttctttcct tcaccaccac ccaggagctc agagagatct aagctgcttt ccatcttttc tcccagcccc aggacactga ctctgtacag gatggggccg tcctcttgcc tccttctcat cctaatcccc cttctccagc tgatcaaccc ggggagtact cagtgttcct tagactccgt tatggataag aagatcaagg atgttctcaa cagtctagag tacagtccct ctcctataag caagaagctc tcgtgtgcta gtgtcaaaag ccaaggcaga ccgtcctcct gccctgctgg gatggctgtc actgctgtgc ttgtggctat ggctgtggtt cgtgggatgt tcagctggaa accaccctgc cactgccagt gcagtgtggt ggactggacc actgcccgac tgctgccacc tgacctgaca gggaggaggc tgagactcag ttttgtgacc atgacagtaa tgaaaccagg gtcccaacca agaaatctaa ctcaaacgtc cacttcattt gttccattcc tgattcttgg gtaataaaga caaactttgt acctctcaaa aaaaaaaaa aaaaagtatt tcattacctc tttctccgca cctggcctgc agccggccgc aggtaagcca gcccaggcct cgccctccag ctaaggcggg acagggc    -3'
```

FIG. 6

Met Gly Pro Ser Ser Cys Leu Leu Leu Ile Leu Ile Pro Leu Leu Gln

Leu Ile Asn Pro Gly Ser Thr Gln Cys Ser Leu Asp Ser Val Met Asp

Lys Lys Ile Lys Asp Val Leu Asn Ser Leu Glu Tyr Ser Pro Ser Pro

Ile Ser Lys Lys Leu Ser Cys Ala Ser Val Lys Ser Gln Gly Arg Pro

Ser Ser Cys Pro Ala Gly Met Ala Val Thr Gly Cys Ala Cys Gly Tyr

Gly Cys Gly Ser Trp Asp Val Gln Leu Glu Thr Thr Cys His Cys Gln

Cys Ser Val Val Asp Trp Thr Thr Ala Arg Cys Cys His Leu Thr

FIG. 7

Met Asp Lys Lys Ile Lys Asp Val Leu Asn Ser Leu Glu Tyr Ser Pro Ser

Pro Ile Ser Lys Lys Leu Ser Cys Ala Ser Val Lys Ser Gln Gly Arg Pro

Ser Ser Cys Pro Ala Gly Met Ala Val Thr Gly Cys Ala Cys Gly Tyr

Gly Cys Gly Ser Trp Asp Val Gln Leu Glu Thr Thr Cys His Cys Gln

Cys Ser Val Val Asp Trp Thr Thr Ala Arg Cys Cys His Leu Thr

FIG. 8

METHODS OF DETECTING A COLON CANCER CELL

CROSS REFERENCE TO RELATED APPLICATION

The present application claims the benefit of U.S. Provisional Application No. 60/200,292, filed Apr. 28, 2000.

STATEMENT AS TO FEDERALLY SPONSORED RESEARCH

Not applicable.

FIELD OF THE INVENTION

The invention relates generally to the fields of molecular biology, genomics, bioinformatics, pathology, and medicine. More particularly, the invention relates to a gene whose expression is modulated in select cancers.

BACKGROUND

With the recent efforts to sequence the entire human genome, the nucleotide sequences of more than 100,000 human genes are expected to be known within the next few years. See, e.g., Robbins, R. J., J. Computat. Biol., 3: 465–478, 1996; Andrade, M. A. and Sander, C., Curr. Opin. Biotechnol., 8: 675–683, 1997; and Collins et al., Science, 282: 682–689, 1998. Once characterized, these genes are anticipated to be useful for identifying new diagnostic and therapeutic targets for a variety of different diseases. Fannon, M. R., Trends Biotechnol., 14: 294–298, 1996. Already several attempts have been made to identify genes or gene products that are uniquely expressed in diseased tissue. The results of these efforts indicated that pathology correlates more often with the pattern of gene expression in the diseased tissue, rather than simply with the absence or presence of a particular gene.

SUMMARY

The invention relates to the discovery of specific polynucleotide sequences that are upregulated in select cancer cells as compared to non-diseased cells. In particular, several expressed sequence tags (ESTs) more prevalent in cancer tissue libraries than in corresponding non-cancerous tissue libraries were identified. These ESTs were then used to identify specific UniGene clusters associated with cancer. See, Schuler, J. Mol. Med. 75(10), 694–698, 1998; Schuler et al., Science 274, 540–546, 1996; and Boguski & Schuler, Nature Genetics 10, 369–371, 1995. Based on the identified polynucleotide sequences, a partial gene sequence termed C4, whose expression is selectively upregulated in colon tumors was identified. Using this partial sequence, a full length gene, termed CCRG (Colon Carcinoma Related Gene) containing the C4 sequence was isolated and sequenced.

An open reading frame of the CCRG gene encodes a polypeptide, i.e., the CCRG protein, which was predicted to have a signal peptide sequence, and putative phosphorylation, myristylation, and glycosylation sites. Based on comparisons to sequences of known function, the nucleotide sequence of CCRG (and C4) was predicted to encode a prokaryotic lipoprotein binding site and a prenylation site. The C-terminus of the CCRG protein is cysteine rich and contains a motif found in ultra high sulphur matrix protein, hair keratin, metallothionein and cation transporters. Using the secondary structure prediction program provided by the ExPASy proteomics server by the Swiss Institute of Bioinformatics (Geneva), CCRG protein was predicted to contain mostly a mixture of alpha helices, beta strands, and coils. The mature CCRG protein has a theoretical molecular weight of 8.62 kDa and a pI of 8.05. These and other analyses indicated that CCRG protein is a colon tumor associated secreted factor.

Accordingly, the invention features a purified nucleic acid present at higher levels in colon cancer cells than in non-cancerous colon cells and includes a nucleotide sequence that encodes a polypeptide sharing at least 80% sequence identity with SEQ ID NO:7 or with a fragment of SEQ ID NO:7 at least 20 residues in length. The nucleotide sequence can be one that defines a polynucleotide whose complement hybridizes under high stringency conditions to the nucleotide sequence of SEQ ID NO:6. The polypeptide encoded by the nucleic acid can have an amino acid sequence consisting of SEQ ID NO:7 or a fragment of SEQ ID NO:7 at least 20 residues in length. The nucleic acid can include a fragment of the polynucleotide sequence of SEQ ID NO:6 at least 50 residues long (e.g., one including the polynucleotide sequence of SEQ ID NO:6).

Also within the invention is a vector including a purified nucleic acid present at higher levels in colon cancer cells than in non-cancerous colon cells, the purified nucleic acid including a nucleotide sequence that encodes a polypeptide sharing at least 80% sequence identity with SEQ ID NO:7 or with a fragment of SEQ ID NO:7 at least 20 residues in length. The nucleic acid contained within this vector can be operably linked to one or more expression control sequences. In another aspect, the invention features a cell including a vector of the invention. including a purified nucleic acid present at higher levels in colon cancer cells than in non-cancerous colon cells.

The invention also provides a probe including an oligonucleotide and a detectable label attached to the oligonucleotide, the oligonucleotide being at least 15 nucleotides in length and hybridizing under high stringency conditions to the nucleotide sequence of SEQ ID NO:7 or a complement of the nucleotide sequence of SEQ ID NO:7.

A kit for detecting a purified nucleic acid including a nucleotide sequence that encodes a polypeptide sharing at least 80% sequence identity with SEQ ID NO:7 or with a fragment of SEQ ID NO:7 at least 20 residues in length in a cell is also within the invention. The kit includes: a first PCR primer including a first nucleic acid molecule including the nucleotide sequence of SEQ ID NO:2 or SEQ ID NO:9, and a second PCR primer including a second nucleic acid molecule including the nucleotide sequence of SEQ ID NO:3 or SEQ ID NO:10.

The invention also features a purified polypeptide expressed at higher levels by colon cancer cells than by non-cancerous colon cells. The purified polypeptide includes an amino acid sequence that shares at least 80% sequence identity with SEQ ID NO:7 or a fragment of SEQ ID NO:7 at least 20 residues in length, e.g., one including a fragment of SEQ ID NO:7 at least 20 residues in length or one including residues 31–111 of the amino acid sequence of SEQ ID NO:7. The purified polypeptide can also include the amino acid sequence of SEQ ID NO:7.

A purified antibody that specifically binds to a polypeptide including an amino acid sequence that shares at least 80% sequence identity with SEQ ID NO:7 or a fragment of SEQ ID NO:7 at least 20 residues in length is featured in the invention. This antibody can include a detectable label.

In further aspect, the invention provides a method of producing a CCRG polypeptide. This method includes the steps of: (a) providing a cell transformed with a purified nucleic acid including a nucleotide sequence that encodes a CCRG polypeptide sharing at least 80% sequence identity with SEQ ID NO:7; (b) culturing the cell under conditions that allow expression of the CCRG polypeptide; and (c) collecting the CCRG polypeptide from the cultured cell.

A screening method for identifying a substance that modulates expression of a gene encoding a CCRG polypeptide sharing at least 80% sequence identity with SEQ ID NO:7 is also within the invention. This method includes the steps of: (a) providing a test cell that includes the gene encoding a CCRG polypeptide sharing at least 80% sequence identity with SEQ ID NO:7; (b) contacting the test cell with a candidate substance; and (c) detecting an increase or decrease in the expression level of the gene encoding the CCRG polypeptide in the presence of the candidate substance, compared to the expression level of the gene encoding CCRG polypeptide in the absence of the candidate substance, as an indication that the candidate substance modulates the level of expression of the gene encoding the CCRG polypeptide.

In addition, the invention provides a method for isolating a substance that binds a CCRG polypeptide sharing at least 80% sequence identity with SEQ ID NO:7. This method includes the steps of: (a) providing a sample of the CCRG polypeptide immobilized on a substrate;(b) contacting a mixture containing the CCRG polypeptide-binding substance with the immobilized CCRG polypeptide; (c) separating unbound components of the mixture from bound components of the mixture; and (d) recovering the CCRG polypeptide-binding substance from the immobilized CCRG polypeptide.

A method for detecting the presence of a CCRG nucleic acid or polypeptide in a biological sample is also included within the invention. This method includes the steps of: (a) providing the biological sample; and (b) detecting the presence of the CCRG nucleic acid or polypeptide in the biological sample. In one variation of this method, step (b) of detecting the presence of the CCRG nucleic acid or polypeptide in a biological sample includes: contacting the biological sample with a probe that binds to the CCRG nucleic acid or polypeptide; and detecting binding of the probe to the biological sample. In another variation of this method, step (b) of detecting the presence of the CCRG nucleic acid or polypeptide in a biological sample includes: isolating RNA from the biological sample; generating cDNAs from the isolated RNA; contacting the cDNAs with a first PCR primer that hybridizes to a first portion of a polynucleotide sharing at least 80% sequence identity with SEQ ID NO:6 or a complement of SEQ ID NO:6, and a second PCR primer that hybridizes to a second portion of a polynucleotide sharing at least 80% sequence identity with SEQ ID NO:6 or a complement of SEQ ID NO:6 to form a mixture; subjecting the mixture to reverse transcriptase-polymerase chain reaction to generate PCR amplification products; and analyzing the PCR amplification products by gel electrophoresis.

Also within the invention is a method for detecting the presence of a colon cancer cell in a biological sample. This method includes the steps of: (a) providing the biological sample; and (b) analyzing the biological sample for the presence of a molecule selected from the group consisting of: a nucleic acid at least 15 nucleotides in length that hybridizes under stringent conditions to the nucleic acid of SEQ ID NO:6 or the complement of SEQ ID NO:6, and a polypeptide sharing at least 80% sequence identity with SEQ ID NO:7. Presence of the molecule in the biological sample indicates that the sample contains a colon cancer cell.

The invention also provides a method for detecting the presence of a CCRG protein in a biological sample. This method includes the steps of: (a) providing the biological sample; and (b) analyzing the biological sample for the presence of a polypeptide including an amino acid sequence that shares at least 80% sequence identity with SEQ ID NO:7 or a fragment of SEQ ID NO:7 at least 20 residues in length. Presence of the polypeptide in the biological sample indicates that the sample contains the CCRG protein. In one variation of this method, the step (b) of analyzing the biological sample for the presence of a polypeptide including an amino acid sequence that shares at least 80% sequence identity with SEQ ID NO:7 or a fragment of SEQ ID NO:7 at least 20 residues in length includes contacting the biological sample with an antibody that specifically binds to a polypeptide including an amino acid sequence that shares at least 80% sequence identity with SEQ ID NO:7 or a fragment of SEQ ID NO:7 at least 20 residues in length.

In the foregoing methods, the biological sample can be a cell derived from a colon (e.g., a human colon), feces, urine, blood, plasma, or serum.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

By the term "gene" is meant a nucleic acid molecule that codes for a particular protein, or in certain cases, a functional or structural RNA molecule. For example, the CCRG gene encodes the CCRG protein.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the terms "CCRG gene," "CCRG polynucleotide," or "CCRG nucleic acid" is meant a native CCRG-encoding nucleic acid sequence, e.g., the native CCRG cDNA (as shown in FIG. 6); a nucleic acid having sequences from which CCRG cDNA can be transcribed; and/or allelic variants and homologs of the foregoing. The terms encompass double-stranded DNA, single-stranded DNA, and RNA.

As used herein, "protein" or "polypeptide" are used synonymously to mean any peptide-linked chain of amino acids, regardless of length or post-translational modification, e.g., glycosylation or phosphorylation. An "purified" polypeptide is one that has been substantially separated or isolated away from other polypeptides in a cell or organism in which the polypeptide naturally occurs (e.g., 30, 40, 50, 60, 70, 80, 90, 95, 96, 97, 98, 99, 100% free of contaminants).

By the terms "CCRG protein" or "CCRG polypeptide" is meant an expression product of an CCRG gene such as the native CCRG protein of FIG. 7 (SEQ ID NO:7) or FIG. 8 (amino acid residues 31–11 of SEQ ID NO:7) or a protein that shares at least 65% (but preferably 75, 80, 85, 90, 95, 96, 97, 98, or 99%) amino acid sequence identity with the protein of FIG. 7 or FIG. 8 and displays a functional activity of CCRG. A "functional activity" of a protein is any activity associated with the physiological function of the protein. For example, functional activities of CCRG may include selective expression in certain neoplastic tissues. In addition, the expression of CCRG in the small intestine suggests that it may be an autocrine secreted growth factor in the intestine and that its overexpression in the large intestine (colon) may contribute to tumor formation.

When referring to a nucleic acid molecule or polypeptide, the term "native" refers to a naturally-occurring (e.g., a "wild-type") nucleic acid or polypeptide. A "homolog" of a CCRG gene is a gene sequence encoding a CCRG polypeptide isolated from an organism other than a human being. Similarly, a "homolog" of a native CCRG polypeptide is an expression product of a CCRG homolog.

A "fragment" of a CCRG nucleic acid is a portion of a CCRG nucleic acid that is less than full-length and comprises at least a minimum length capable of hybridizing specifically with a native CCRG nucleic acid under stringent hybridization conditions. The length of such a fragment is preferably at least 15 nucleotides, more preferably at least 20 nucleotides, and most preferably at least 30 nucleotides of a native CCRG nucleic acid sequence. A "fragment" of a CCRG polypeptide is a portion of a CCRG polypeptide that is less than full-length (e.g., a polypeptide consisting of 5, 10, 15, 20, 30, 40, 50, 75, 100 or more amino acids of native CCRG polypeptide), and preferably retains at least one functional activity of native CCRG polypeptide. For example, a polypeptide consisting of amino acids 31–111 of the native CCRG polypeptide (i.e., the polypeptide of SEQ ID NO:7 without the signal peptide) is a fragment of the full length native CCRG polypeptide.

When referring to hybridization of one nucleic to another, "low stringency conditions" means in 10% formamide, 5×Denhart's solution, 6×SSPE, 0.2% SDS at 42° C., followed by washing in 1×SSPE, 0.2% SDS, at 50° C.; "moderate stringency conditions" means in 50% formamide, 5×Denhart's solution, 5×SSPE, 0.2% SDS at 42° C., followed by washing in 0.2×SSPE, 0.2% SDS, at 65° C.; and "high stringency conditions" means in 50% formamide, 5×Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. As another example, if 12 positions in a protein sequence 20 amino acids in length are identical to the corresponding positions in a second 20-amino acid sequence, then the two sequences have 60% sequence identity. Preferably, the length of the compared nucleic acid sequences is at least 60 nucleotides, more preferably at least 75 nucleotides, and most preferably 100 nucleotides; and the length of compared polypeptide sequences is at least 15, 25, and 50 amino acids. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute of one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with another amino acid having similar characteristics. Examples of conservative amino acid substitutions are ser for ala, thr, or cys; lys for arg; gin for asn, his, or lys; his for asn; glu for asp or lys; asn for his or gin; asp for glu; pro for gly; leu for ile, phe, met, or val; val for ile or leu; ile for leu, met, or val; arg for lys; met for phe; tyr for phe or trp; thr for ser; trp for tyr; and phe for tyr.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors."

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic." "A "transgenic" or "transformed" cell or organism (e.g., a mammal) also includes progeny of the cell or organism. For example, an organism transgenic for CCRG is one in which CCRG nucleic acid has been introduced.

By the term "CCRG-specific antibody" is meant an antibody that binds a CCRG protein (e.g., a protein having the amino acid sequence of SEQ ID NO:7), and displays no substantial binding to other naturally occurring proteins other than those sharing the same antigenic determinants as a CCRG protein. The term includes polyclonal and monoclonal antibodies.

As used herein, "bind," "binds," or "interacts with" means that one molecule recognizes and adheres to a particular second molecule in a sample, but does not substantially recognize or adhere to other structurally unrelated molecules in the sample. Generally, a first molecule that specifically binds" a second molecule has a binding affinity greater than about $10^5$ to $10^6$ moles/liter for that second molecule.

The term "labeled," with regard to a probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and the further advantages of this invention may be better understood by referring to the following description taken in conjunction with the accompanying drawings, in which:

FIG. 6 is the nucleotide sequence of the native CCRG gene.

FIG. 7 is the amino acid sequence of the processed form (i.e., without the signal peptide) of native CCRG protein.

FIG. 8 is the amino acid sequence of the unprocessed form (i.e., with the signal peptide) of native CCRG protein.

DETAILED DESCRIPTION

Figure 1:
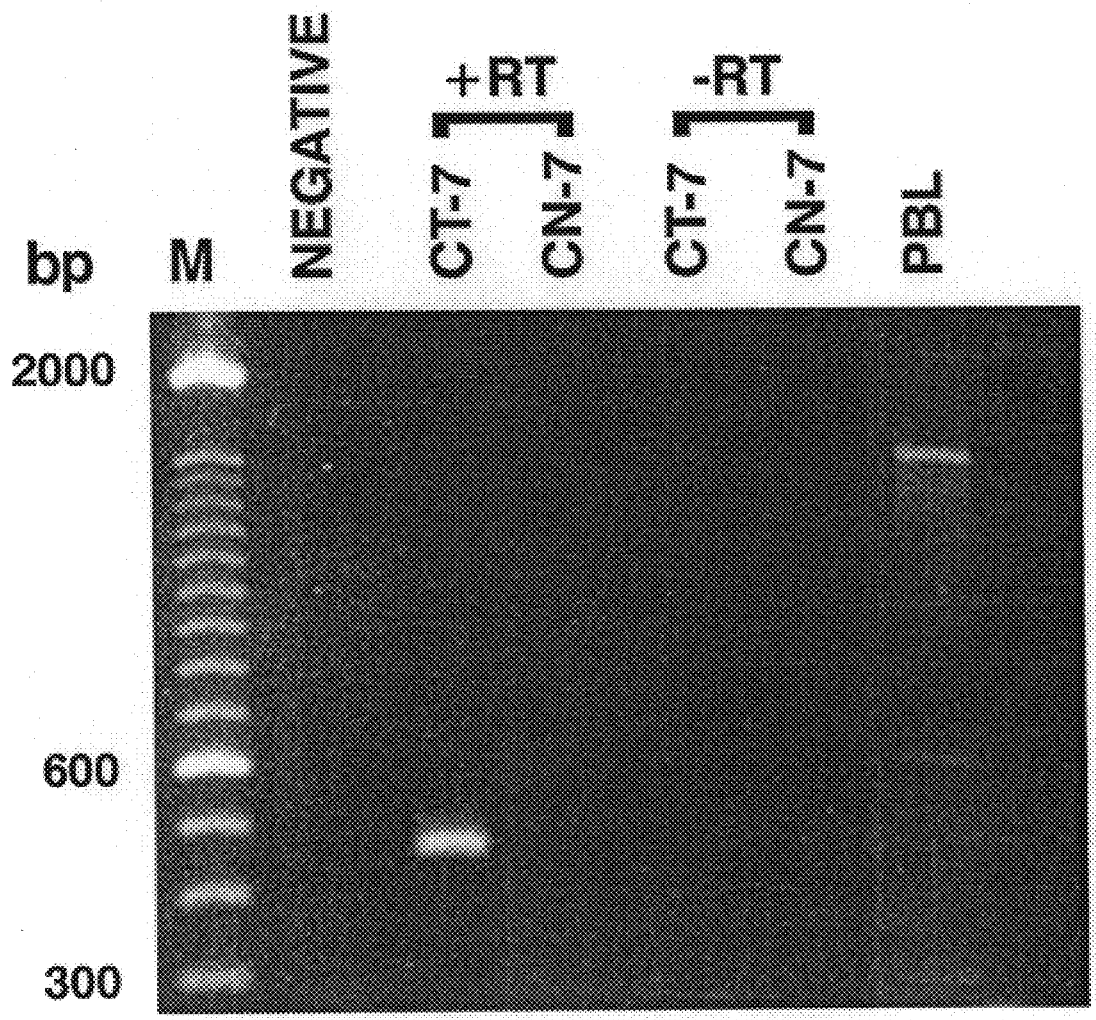
FIG. 1 is a photograph of an ethidium bromide-stained agarose gel after electrophoresis of cDNAs from a matched set of tumor and normal tissues. The tissues were analyzed for expression of CCRG (C4) and actin gene. M=100 bp ladder; negative=template minus control; +/−RT=cDNAs made in the presence or absence of reverse transcriptase; PBL=genomic DNA from peripheral blood lymphocytes.

The invention encompasses compositions and methods relating to the CCRG gene, a human gene associated with cancer. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, ©1991, Whitehead Institute for Biomedical Research, Cambridge, MA.). The Reverse Transcriptase Polymerase Chain Reaction (RT-PCR) method used to identify and amplify certain polynuleotide sequences within the invention was performed as described in Elek et al., In Vivo, 14:172–182, 2000). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Nucleic Acids Encoding CCRG

The present invention utilizes the human CCRG gene, which has now been cloned and sequenced. A preferred nucleic acid molecule of for use in the invention is the native CCRG polynucleotide shown in FIG. 6 (SEQ ID NO:6) and deposited with Genbank as Accession No. AF323921. The clone G6 containing the full length CCRG gene (SEQ ID NO:6) in the PEAK 8 expression vector (Edge Biosystems) was deposited with the American Type Culture Collection (Rockville, Md.) as Accession No. PTA-2739 on November 30, 2000. Another nucleic acid that can be used in various aspects of the invention includes a purified nucleic acid (polynucleotide) that encodes a polypeptide having either the amino acid sequence of FIG. 7 (SEQ ID NO:7) or the amino acid sequence of FIG. 8 (amino acid residues 31–111 of SEQ ID NO:7). As the native CCRG gene was originally cloned from a small intestine, cDNA library nucleic acid molecules encoding a polypeptide of the present invention can be obtained from such a library or from any human colon tumor tissue itself by conventional cloning methods such as those described herein.

Nucleic acid molecules utilized in the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes the native CCRG protein may be identical to the nucleotide sequence shown in FIG. 6 (SEQ ID NO:6). It may also be a different coding sequence which, as a result of the redundancy or degeneracy of the genetic code, encodes the same polypeptide as the polynucleotide of SEQ ID NO:6.

Other nucleic acid molecules within the invention are variants of the native CCRG gene such as those that encode fragments (e.g., post-translationally processed forms of), analogs and derivatives of a native CCRG protein. Such variants may be, e.g., a naturally occurring allelic variant of the native CCRG gene, a homolog of the native CCRG gene, or a non-naturally occurring variant of the native CCRG gene. These variants have a nucleotide sequence that differs from the native CCRG gene in one or more bases. For example, the nucleotide sequence of such variants can feature a deletion, addition, or substitution of one or more nucleotides of the native CCRG gene. Nucleic acid insertions are preferably of about 1 to 10 contiguous nucleotides, and deletions are preferably of about 1 to 30 contiguous nucleotides.

In other applications, variant CCRG proteins displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of the native CCRG gene within the invention are nucleic acids isolated from human tissue that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native CCRG gene, and encode polypeptides having structural similarity to native CCRG protein. Homologs of the native CCRG gene within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native CCRG gene, and encode polypeptides having structural similarity to native CCRG protein. Public and/or proprietary nucleic acid databases can be searched in an attempt to identify other nucleic acid molecules having a high percent (e.g., 70, 80, 90% or more) sequence identity to the native CCRG gene.

Non-naturally occurring CCRG gene variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native CCRG gene, and encode polypeptides having structural similarity to native CCRG protein. Examples of non-naturally occurring CCRG gene variants are those that encode a fragment of a CCRG protein, those that hybridize to the native CCRG gene or a complement of to the native CCRG gene under stringent conditions, those that share at least 65% sequence identity with the native CCRG gene or a complement of the native CCRG gene, and those that encode a CCRG fusion protein.

Nucleic acids encoding fragments of native CCRG protein within the invention are those that encode, e.g., 2, 5, 10, 25, 30, 40, 50, 60, 70, 80, 90, 100, or more amino acid residues of the native CCRG protein. Shorter oligonucleotides (e.g., those of 6, 7, 8, 9, 10, 11, 12, 13, 14, 15, 16, 17, 18, 19, 20, 30, 50, 100, base pairs in length) that encode or hybridize with nucleic acids that encode fragments of the native CCRG protein can be used as probes, primers, or antisense molecules. Longer polynucleotides (e.g., those of 125, 150, 175, 200, 225, 250, 275, 300, or more base pairs) that encode or hybridize with nucleic acids that encode fragments of native CCRG protein can also be used in various aspects of the invention. Nucleic acids encoding fragments of native CCRG protein can be made by enzymatic digestion (e.g., using a restriction enzyme) or chemical degradation of the full length native CCRG gene or variants thereof.

Nucleic acids that hybridize under stringent conditions to the nucleic acid of SEQ ID NO:6 or the complement of SEQ ID NO:6 can also be used in the invention. For example, such nucleic acids can be those that hybridize to SEQ ID NO:6 or the complement of SEQ ID NO:6 under low stringency conditions, moderate stringency conditions, or high stringency conditions are within the invention. Preferred such nucleotide acids are those having a nucleotide sequence that is the complement of all or a portion of SEQ ID NO:6. Other variants of the native CCRG gene within the invention are polynucleotides that share at least 65% (e.g., 65, 70, 75, 80, 85, 90, 91, 92, 93, 94, 95, 96, 97, 98, and 99%) sequence identity to SEQ ID NO:6 or the complement of SEQ ID NO:6. Nucleic acids that hybridize under stringent conditions to or share at least 65% sequence identity with SEQ ID NO:6 or the complement of SEQ ID NO:6 can be obtained by techniques known in the art such as by making mutations in the native CCRG gene, or by isolation from an organism expressing such a nucleic acid (e.g., an allelic variant).

Nucleic acid molecules encoding CCRG fusion proteins are also within the invention. Such nucleic acids can be made by preparing a construct (e.g., an expression vector) that expresses a CCRG fusion protein when introduced into a suitable host. For example, such a construct can be made by ligating a first polynucleotide encoding a CCRG protein fused in frame with a second polynucleotide encoding another protein (e.g., a detectable label or a cytotoxin) such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553–6556; Lemaitre et al. (1987) Proc. Natl. Acad. Sci. USA 84:648–652; PCT Publication No. WO 88/09810, published Dec. 15, 1988), hybridization-triggered cleavage agents. (See, e.g., Krol et al. (1988) BioTechniques 6:958–976) or intercalating agents. (See, e.g, Zon (1988) Pharm. Res. 5:539–549). To this end, the oligonucleotides may be conjugated to another molecule, e.g., a peptide, hybridization triggered cross-linking agent, transport agent, hybridization-triggered cleavage agent, etc.

Using the nucleotide of the native CCRG gene and the amino acid sequence of a native CCRG protein, those skilled in the art can create nucleic acid molecules that have minor variations in their nucleotide, by, for example, standard nucleic acid mutagenesis techniques or by chemical synthesis. Variant CCRG nucleic acid molecules can be expressed to produce variant CCRG proteins.

Antisense, Ribozyme, Triplex Techniques

Another aspect of the invention relates to the use of purified antisense nucleic acids to inhibit expression of CCRG. Antisense nucleic acid molecules within the invention are those that specifically hybridize (e.g. bind) under cellular conditions to cellular mRNA and/or genomic DNA encoding a CCRG protein in a manner that inhibits expression of the CCRG protein, e.g., by inhibiting transcription and/or translation. The binding may be by conventional base pair complementarity, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes a CCRG protein. Alternatively, the antisense construct can take the form of an oligonucleotide probe generated ex vivo which, when introduced into a CCRG protein expressing cell, causes inhibition of CCRG protein expression by hybridizing with an mRNA and/or genomic sequences coding for CCRG protein. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of a CCRG protein encoding nucleotide sequence, are preferred.

Antisense approaches involve the design of oligonucleotides (either DNA or RNA) that are complementary to CCRG mRNA. The antisense oligonucleotides will bind to CCRG mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. (Wagner, R. (1994) Nature 372:333). Therefore, oligonucleotides complementary to either the 5' or 3' untranslated, non-coding regions of a CCRG gene could be used in an antisense approach to inhibit translation of endogenous CCRG mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of CCRG mRNA, antisense nucleic acids should be at least eighteen nucleotides in length (e.g., 18, 20, 25, 30, 35, 40, 45, 50, 60, 70, 80, 90 nucleotides in length), and are preferably less that about 100 nucleotides in length. An exemplary antisense oligonucleotide is an olignucleotide that is the complement of the olignucleotide shown herein as SEQ ID NO:5. For example, an oligonucleotide having the nucleotide sequence of 5' TCC TTG ATC TTC TTA TCC ATA ACG 3' (SEQ ID NO:8) could be used as an antisense oligonucleotide.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Antisense oligonucleotides of the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxyethyl) uracil, 5-carboxymethylaminomethyl-2-thiouridine, 5-carboxymethylaminomethyluracil, dihydrouricil, beta-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Antisense oligonucleotides of the invention may also comprise at least one modified sugar moiety selected from the group including but not limited to arabinose, 2-fluoroarabinose, xylulose, and hexose; and may additionally include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al. (1987) Nucl. Acids Res. 15:6625–6641). Such oligonucleotide can be a 2'-0-methylribonucleotide (Inoue et al. (1987) Nucl. Acids Res. 15:6131–6148), or a chimeric RNA-DNA analogue (Inoue et al. (1987) FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209), and methylphosphonate oligonucleotides can be prepared by use of controlled pore glass polymer supports (Sarin et al. (1988) Proc. Natl. Acad. Sci. U.S.A. 85:7448–7451).

The antisense molecules should be delivered into cells that express CCRG in vivo. A number of methods have been developed for delivering antisense DNA or RNA into cells. For instance, antisense molecules can be introduced directly into the tissue site by such standard techniques as electroporation, liposome-mediated transfection, CaCl-mediated transfection, or the use of a gene gun. Alternatively, modified antisense molecules, designed to target the desired cells (e.g., antisense linked to peptides or antibodies that specifically bind receptors or antigens expressed on the target cell surface) can be used.

Because it is often difficult to achieve intracellular concentrations of the antisense sufficient to suppress translation on endogenous mRNAs, a preferred approach utilizes a recombinant DNA construct in which the antisense oligonucleotide is placed under the control of a strong promoter (e.g., the CMV promoter). The use of such a construct to transform cells will result in the transcription of sufficient amounts of single stranded RNAs that will form complementary base pairs with the endogenous CCRG transcripts and thereby prevent translation of CCRG mRNA.

Ribozyme molecules designed to catalytically cleave CCRG mRNA transcripts can also be used to prevent translation of CCRG mRNA and expression of CCRG protein (See, e.g., PCT Publication No. WO 90/11364, published Oct. 4, 1990; Sarver et al. (1990) Science 247:1222–1225 and U.S. Pat. No. 5,093,246). While ribozymes that cleave mRNA at site specific recognition sequences can be used to destroy CCRG mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585–591. There are several potential hammerhead ribozyme cleavage sites within the nucleotide sequence of the native CCRG gene. Preferably the ribozyme is engineered so that the cleavage recognition site is located near the 5' end of CCRG mRNA; i.e., to increase efficiency and minimize the intracellular accumulation of non-functional mRNA transcripts. Ribozymes within the invention can be delivered to a cell using a vector as described below.

Endogenous CCRG gene expression can also be reduced by inactivating or "knocking out" the CCRG gene or its promoter using targeted homologous recombination. See, e.g, Kempin et al., Nature 389: 802 (1997); Smithies et al. (1985) Nature 317:230–234; Thomas and Capecchi (1987) Cell 51:503–512; and Thompson et al. (1989) Cell 5:313–321. For example, a mutant, non-functional CCRG gene variant (or a completely unrelated DNA sequence) flanked by DNA homologous to the endogenous CCRG gene (either the coding regions or regulatory regions of the CCRG gene) can be used, with or without a selectable marker and/or a negative selectable marker, to transfect cells that express CCRG protein in vivo.

Alternatively, endogenous CCRG gene expression might be reduced by targeting deoxyribonucleotide sequences complementary to the regulatory region of the CCRG gene (i.e., the CCRG promoter and/or enhancers) to form triple helical structures that prevent transcription of the CCRG gene in target cells. (See generally, Helene, C. (1991) Anticancer Drug Des. 6(6):569–84; Helene, C., et al. (1992) Ann. N.Y. Acad. Sci. 660:27–36; and Maher, L. J. (1992) Bioassays 14(12):807–15.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Probes and Primers

The invention also includes oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by the polymerase chain reaction (PCR) or other conventional nucleic-acid amplification methods. Probes and primers within the invention are generally 15 nucleotides or more in length, preferably 20 nucleotides or more, more preferably 25 nucleotides, and most preferably 30 nucleotides or more. Preferred probes and primers are those that hybridize to the native CCRG gene sequence under high stringency conditions, and those that hybridize CCRG gene homologs under at least moderate stringency conditions. Preferably, probes and primers according to the present invention have complete sequence identity with the native CCRG gene sequence, although probes differing from the native CCRG gene sequence and that retain the ability to hybridize to native CCRG gene sequences under stringent conditions may be designed by conventional methods. Primers and probes based on the native CCRG gene sequences disclosed herein can be used to confirm (and, if necessary, to correct) the disclosed native CCRG gene sequence by conventional methods, e.g., by re-cloning and sequencing a native CCRG cDNA. Particularly preferred primer pairs for use in the invention are shown as SEQ ID NO:2 and SEQ ID NO:3; and SEQ ID NO:9 and SEQ ID NO:10, both pairs having been shown to selectively amplify CCRG gene sequences, the former amplifying a 455 bp product, the latter amplifying a 267 bp product including the signal sequence and most of the CDS of the CCRG gene. A particularly preferred oligonucleotide probe for use in the invention is shown as SEQ ID NO:4.

CCRG Proteins

In other aspects, the present invention utilizes a purified CCRG protein encoded by a nucleic acid of the invention. Preferred forms of CCRG protein include a purified native CCRG protein that has either the deduced amino acid sequence shown in FIG. 7 (SEQ ID NO:7) or the amino acid sequence shown in FIG. 8. Variants of native CCRG proteins such as fragments, analogs and derivatives of native CCRG are also within the invention. Such variants include, e.g., a polypeptide encoded by a naturally occurring allelic variant of native CCRG gene, a polypeptide encoded by a homolog of native CCRG gene, and a polypeptide encoded by a non-naturally occurring variant of native CCRG gene.

CCRG protein variants have a peptide sequence that differs from a native CCRG protein in one or more amino acids. The peptide sequence of such variants can feature a deletion, addition, or substitution of one or more amino acids of a native CCRG polypeptide. Amino acid insertions are preferably of about 1 to 4 contiguous amino acids, and deletions are preferably of about 1 to 10 contiguous amino acids. In some applications, variant CCRG proteins substantially maintain a native CCRG protein functional activity (e.g., association with cancer). For other applications, variant CCRG proteins lack or feature a significant reduction in a CCRG protein functional activity. Where it is desired to retain a functional activity of native CCRG protein, preferred CCRG protein variants can be made by expressing nucleic acid molecules within the invention that feature silent or conservative changes. Variant CCRG proteins with substantial changes in functional activity can be made by expressing nucleic acid molecules within the invention that feature less than conservative changes.

CCRG protein fragments corresponding to one or more particular motifs and/or domains or to arbitrary sizes, for example, at least 5, 10, 25, 30, 40, 50, 50, 70, 75, 80, 90, and 100 amino acids in length are within the scope of the present invention. Isolated peptidyl portions of CCRG proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a CCRG protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of native CCRG protein.

Another aspect of the present invention concerns recombinant forms of the CCRG proteins. Recombinant polypeptides preferred by the present invention, in addition to native CCRG protein, are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of SEQ ID NO:6. In a preferred embodiment, variant CCRG proteins have one or more functional activities of native CCRG protein.

CCRG protein variants can be generated through various techniques known in the art. For example, CCRG protein variants can be made by mutagenesis, such as by introducing discrete point mutation(s), or by truncation. Mutation can give rise to a CCRG protein variant having substantially the same, or merely a subset of the functional activity of a native CCRG protein. Alternatively, antagonistic forms of the protein can be generated which are able to inhibit the function of the naturally occurring form of the protein, such as by competitively binding to another molecule that interacts with a CCRG protein. In addition, agonistic forms of the protein may be generated that constitutively express one or more CCRG functional activities. Other variants of CCRG that can be generated include those that are resistant to proteolytic cleavage, as for example, due to mutations which alter protease target sequences. Whether a change in the amino acid sequence of a peptide results in a CCRG protein variant having one or more functional activities of native CCRG protein can be readily determined by testing the variant for a native CCRG protein functional activity.

As another example, CCRG protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential CCRG protein sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) Proc. Natl. Acad. Sci. USA 89:2429–2433; Devlin et al. (1990) Science 249: 404–406; Cwirla et al. (1990) Proc. Natl. Acad. Sci. USA 87: 6378–6382; as well as U.S. Pat. Nos. 5,223,409; 5,198,346; and 5,096,815).

Similarly, a library of coding sequence fragments can be provided for a CCRG gene clone in order to generate a variegated population of CCRG protein fragments for screening and subsequent selection of fragments having one or more native CCRG functional activities. A variety of techniques are known in the art for generating such libraries, including chemical synthesis. In one embodiment, a library of coding sequence fragments can be generated by (i) treating a double-stranded PCR fragment of a CCRG gene coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with SI nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of CCRG gene variants. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, techniques such as recursive ensemble mutagenesis (REM) that allow one to avoid the very high proportion of non-functional proteins in a random library and simply enhance the frequency of functional proteins (thus decreasing the complexity required to achieve a useful sampling of sequence space) can be used. REM is an algorithm which enhances the frequency of functional mutants in a library when an appropriate selection or screening method is employed (Arkin and Yourvan (1992) Proc. Natl. Acad. Sci. USA 89:7811–7815; Yourvan et al. (1992) Parallel Problem Solving from Nature, 2., In Maenner and Manderick, eds., Elsevier Publishing Co., Amsterdam, pp. 401–410; Delgrave et al. (1993) Protein Engineering 6(3):327–331).

The invention also provides for reduction of CCRG proteins to generate mimetics, e.g. peptide or non-peptide agents, that are able to disrupt binding of a CCRG protein to other proteins or molecules with which a native CCRG protein interacts. Thus, the mutagenic techniques described can also be used to map which determinants of a CCRG protein participate in protein-protein interactions involved in, for example, binding of a CCRG protein to other proteins which may function upstream (including both activators and repressors of its activity) of the CCRG protein or to proteins or nucleic acids which may function downstream of the CCRG protein, and whether such molecules are positively or negatively regulated by the CCRG protein. To illustrate, the critical residues of a CCRG protein which are involved in molecular recognition of, for example, a molecule having a moiety that binds the CCRG protein can be determined and used to generate CCRG protein-derived peptidomimetics which competitively inhibit binding of CCRG protein with that moiety. By employing, for example, scanning mutagenesis to map the amino acid residues of a CCRG protein that are involved in binding other proteins, peptidomimetic compounds can be generated which mimic those residues of native CCRG protein. Such mimetics may then be used to interfere with the normal function of a CCRG protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill, 1985), beta-turn dipeptide cores (Nagai et al. (1985) Tetrahedron Lett26:647;and Satoetal. (1986) J. Chem. Soc. Perkin. Trans. 1:1231),andb-aminoalcohols (Gordon et al. (1985) Biochem. Biophys. Res. Commun. 126:419; and Dann et al. (1986) Biochem. Biophys. Res. Commun. 134:71). CCRG proteins may also be chemically modified to create CCRG derivatives by forming covalent or aggregate conjugates with other chemical moieties, such as glycosyl groups, lipids, phosphate, acetyl groups and the like. Covalent derivatives of CCRG protein can be prepared by linking the chemical moieties to functional groups on amino acid side chains of the protein or at the N-terminus or at the C-terminus of the polypeptide.

The present invention further pertains to methods of producing the subject CCRG proteins. For example, a host cell transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant CCRG protein can be isolated from host cells using techniques known in the art for purifying proteins including ion-exchange chromatography, gel filtration chromatography, ultrafiltration, electrophoresis, and immunoaffinity purification with antibodies specific for such protein.

For example, after CCRG protein has been expressed in a cell, it can be isolated using any immuno-affinity chromatography. For instance, an anti-CCRG antibody (e.g., produced as described below) can be immobilized on a column chromatography matrix, and the matrix can be used for immuno-affinity chromatography to purify CCRG protein from cell lysates by standard methods (see, e.g., Ausubel et al., supra). After immuno-affinity chromatography, CCRG protein can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, CCRG protein is expressed as a fusion protein containing an affinity tag (e.g., GST) that facilitates its purification.

CCRG-protein Specific Antibodies

CCRG proteins (or immunogenic fragments or analogs thereof) can be used to raise antibodies useful in the invention. Such proteins can be produced by recombinant techniques or synthesized as described above. In general, CCRG proteins can be coupled to a carrier protein, such as KLH, as described in Ausubel et al., supra, mixed with an adjuvant, and injected into a host animal. Antibodies produced in that animal can then be purified by peptide antigen affinity chromatography. In particular, various host animals can be immunized by injection with a CCRG protein or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and Corynebacterium parvum.

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the CCRG proteins described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Human or humanoid antibodies that specifically bind a CCRG protein can also be produced using known methods. For example, human antibodies against CCRG protein can be made by adapting known techniques for producing human antibodies in animals such as mice. See, e.g., Fishwild, D. M. et al., Nature Biotechnology 14 (1996): 845–851; Heijnen, I. et al., Journal of Clinical Investigation 97 (1996): 331–338; Lonberg, N. et al., Nature 368 (1994): 856–859; Morrison, S. L., Nature 368 (1994): 812–813; Neuberger, M., Nature Biotechnology 14 (1996): 826; and U.S. Pat. Nos. 5,545,806; 5,569,825; 5,877,397; 5,939,598; 6,075,181; 6,091,001; 6,114,598; and 6,130,314. Humanoid antibodies against CCRG can be made from non-human antibodies by adapting known methods such as those described in U.S. Pat. Nos. 5,530, 101; 5,585,089; 5,693, 761; and 5,693,762.

Once produced, polyclonal or monoclonal antibodies can be tested for specific CCRG recognition by Western blot or immunoprecipitation analysis by standard methods, for example, as described in Ausubel et al., supra. Antibodies that specifically recognize and bind to CCRG are useful in the invention. For example, such antibodies can be used in an immunoassay to monitor the level of CCRG produced by a mammal (e.g., to determine the amount or subcellular location of CCRG).

Preferably, CCRG protein selective antibodies of the invention are produced using fragments of the CCRG protein that lie outside highly conserved regions and appear likely to be antigenic, by criteria such as high frequency of charged residues. Cross-reactive anti-CCRG protein antibodies are produced using a fragment of a CCRG protein that is conserved among members of this family of proteins. In one specific example, such fragments are generated by standard techniques of PCR, and are then cloned into the pGEX expression vector (Ausubel et al., supra). Fusion proteins are expressed in E. coli and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant CCRG proteins or control proteins, such as glucocorticoid receptor, CAT, or luciferase.

The antibodies of the invention can be used, for example, in the detection of CCRG protein in a biological sample. Antibodies also can be used in a screening assay to measure the effect of a candidate compound on expression or localization of CCRG protein. Additionally, such antibodies can be used to interfere with the interaction of CCRG protein and other molecules that bind CCRG protein.

Techniques described for the production of single chain antibodies (e.g., U.S. Pat. Nos. 4,946,778, 4,946,778, and 4,704,692) can be adapted to produce single chain antibodies against a CCRG protein, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

Proteins that Associate with CCRG

The invention also features methods for identifying polypeptides that can associate with a CCRG protein. Any method that is suitable for detecting protein-protein interactions can be employed to detect polypeptides that associate with a CCRG protein. Among the traditional methods that can be employed are co-immunoprecipitation, crosslinking, and co-purification through gradients or chromatographic columns of cell lysates or proteins obtained from cell lysates and the use of a CCRG protein to identify proteins in the lysate that interact with a CCRG protein. For these assays, the CCRG protein can be a full length CCRG protein, a particular domain of CCRG protein, or some other suitable CCRG protein. Once isolated, such an interacting protein can be identified and cloned and then used, in conjunction with standard techniques, to alter the activity of the CCRG protein with which it interacts. For example, at least a portion of the amino acid sequence of a protein that interacts with CCRG protein can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel et al., supra; and Innis et al., supra).

Additionally, methods can be employed that result directly in the identification of genes that encode proteins that interact with a CCRG protein. These methods include, for example, screening expression libraries, in a manner similar to the well known technique of antibody probing of lgt11 libraries, using a labeled CCRG protein or a CCRG fusion protein, for example, a CCRG protein or domain fused to a marker such as an enzyme, fluorescent dye, a luminescent protein, or to an IgFc domain.

There are also methods available that can detect protein-protein interaction in vivo. For example, as described herein the two-hybrid system can be used to detect such interactions in vivo. See, e.g., Chien et al., Proc. Natl. Acad. Sci. USA 88:9578, 1991. Briefly, as one example of utilizing such a system, plasmids are constructed that encode two hybrid proteins: one plasmid includes a nucleotide sequence encoding the DNA-binding domain of a transcription activator protein fused to a nucleotide sequence encoding a native CCRG protein, a CCRG protein variant, or a CCRG fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, a CCRG protein may be used as the bait. Total genomic or cDNA sequences are fused to the DNA encoding an activation domain. This library and a plasmid encoding a hybrid of a bait CCRG protein fused to the DNA-binding domain are co-transformed into a yeast reporter strain, and the resulting transformants are screened for those that express the reporter gene. For example, a bait CCRG gene sequence, such as that encoding CCRG protein or a domain of CCRG protein can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with a bait CCRG protein are to be detected can be made using methods routinely practiced in the art. According to the particular system described herein, for example, the cDNA fragments can be inserted into a vector such that they are translationally fused to the transcriptional activation domain of GAL4. This library can be co-transformed along with the CCRG-GAL4 encoding fusion plasmid into a yeast strain which contains a lacZ gene driven by a promoter which contains GAL4 activation sequence. A cDNA encoded protein, fused to GAL4 transcriptional activation domain, that interacts with bait CCRG protein will reconstitute an active GAL4 protein and thereby drive expression of the HIS3 gene. Colonies that express HIS3 can then be purified from these strains and used to produce and isolate bait CCRG protein-interacting proteins using techniques routinely practiced in the art.

Detection of CCRG Polynucleotides and Proteins

The invention encompasses methods for detecting the presence of a CCRG protein or a CCRG nucleic acid in a biological sample as well as methods for measuring the level of a CCRG protein or a CCRG nucleic acid in a biological sample. Such methods are useful for diagnosing cancer associated with CCRG expression (e.g., colon cancer).

An exemplary method for detecting the presence or absence of CCRG in a biological sample involves obtaining a biological sample from a test subject (e.g., a human patient), contacting the biological sample with a compound or an agent capable of detecting a CCRG protein or a nucleic acid encoding a CCRG protein (e.g., mRNA or genomic DNA), and analyzing binding of the compound or agent to the sample after washing. Those samples having specifically bound compound or agent are those that express a CCRG protein or a nucleic acid encoding a CCRG protein.

A preferred agent for detecting a nucleic acid encoding a CCRG protein is a labeled nucleic acid probe capable of hybridizing (e.g., under stringent hybridization conditions) to the nucleic acid encoding the CCRG protein. The nucleic acid probe can be, for example, all or a portion of the native CCRG gene itself (e.g., a nucleic acid molecule having the sequence of SEQ ID NO:6) or all or a portion of a complement of the native CCRG gene. Similarly, the probe can also be all or a portion of a CCRG gene variant, or all or a portion of a complement of a CCRG gene variant. For instance, oligonucleotides at least 15, 30, 50, 75, 100, 125, 150, 175, 200, 225, or 250 nucleotides in length that specifically hybridize under stringent conditions to the native CCRG gene or a complement of the native CCRG gene can be used as probes within the invention. An exemplary probe has the nucleotide sequence of SEQ ID NO:4. A preferred agent for detecting a CCRG protein is an antibody capable of binding to a CCRG protein, preferably an antibody with a detectable label. Such antibodies can be polyclonal, or more preferably, monoclonal. An intact antibody, or a fragment thereof (e.g., Fab or F(ab')$_2$) can be used.

Detection methods of the invention can be used to detect an mRNA encoding a CCRG protein, a genomic DNA encoding a CCRG protein, or a CCRG protein in a biological sample in vitro as well as in vivo. For example, in vitro techniques for detection of mRNAs encoding a CCRG protein include Northern hybridizations and in situ hybridizations. In vitro techniques for detection of a CCRG protein include enzyme linked immunosorbent assays (ELISAs), Western blots, immunoprecipitations and immunofluorescence. In vitro techniques for detection of genomic DNA encoding a CCRG protein include Southern hybridizations. In vivo techniques for detection of a CCRG protein include introducing a labelled anti-CCRG antibody into a biological sample or test subject. For example, the antibody can be labeled with a radioactive marker whose presence and location in a biological sample or test subject can be detected by standard imaging techniques.

Screening for Compounds that Interact with CCRG Protein

The invention also encompasses methods for identifying compounds that specifically bind to a CCRG protein. One such method involves the steps of providing immobilized purified CCRG protein and at least one test compound; contacting the immobilized protein with the test compound; washing away substances not bound to the immobilized protein; and detecting whether or not the test compound is bound to the immobilized protein. Those compounds remaining bound to the immobilized protein are those that specifically interact with the CCRG protein.

EXAMPLES

The present invention is further illustrated by the following specific examples. The examples are provided for illustration only and are not to be construed as limiting the scope or content of the invention in any way.

Example 1

Identification of Unigene Preferentially Expressed in Colon Tumors

Unigene Hs. 105470 was identified as being present in the colon tumor tissues, but not in the normal tissue. Total RNA was isolated from a matched set of normal and colon tumors and reverse transcribed using random hexamers and Superscript reverse transcriptase (Life Technologies). One-fortieth of the resulting cDNAs was PCR-amplified using the PCR primers described herein as SEQ ID Nos: 2 and 3. The conditions for the PCR included 1) initial denaturation at 94° C. for 7 mins; 2) denaturation at 94° C. for 1 min, annealing at 62° C. for 2 mins. And extension at 72° C. for 3 mins, for 35 cycles with a final extension at 72° C. for 10 mins. Referring to FIG. 1, Unigene Hs 105470 showed a RT-dependant PCR product of 455 bp. This product was not seen in the control RT-minus reaction, nor in the peripheral blood lymphocyte DNA. A product of higher molecular weight was detected in the genomic DNA sample, indicating that the RT-PCR primers reside in two different exons. UniGene # 105470 has five ESTs assigned to the cluster. The sequence of the longest EST (Genbank Accession No. AA524300) in this UniGene is 577 bp in length (which was the maximum size extendable as a contig) and is shown herein as SEQ ID NO:1. The RT-PCR primers used to identify a gene encompassing this EST, termed CCRG, is shown in SEQ ID NO:2 (sense) and SEQ ID NO:3 (antisense).

Example 2

Cloning of the CCRG Gene

A mixture of cDNA libraries from different human tissues (activated T cells, adrenal gland, fetal brain, pituitary glands, spinal cord, small intestine, skeletal muscle, uterus, stomach and trachea) was screened using the oligonucleotide of SEQ ID NO:1 as a probe. Using Edge Sequence as a cloning system, several independent clones were obtained. Clones were verified to contain the CCRG gene by RT-PCR using SEQ ID Nos: 2 and 3 as PCR primers. A predominate 744 bp clone was sequenced. This clone contained the original sequence of SEQ ID NO:1 and 220 bp of additional sequences. A northern blot analysis of total RNA from colon tumor and normal tissue with this 744 bp probe detected a mRNA of approximately 0.8 kb in the tumor, but not in the normal tissue. The nucleotide sequence of this partial cDNA encoding a portion of the CCRG gene, termed C4, is shown as SEQ ID NO:5.

Unamplified human cDNA libraries from activated T cells, adrenal gland, fetal HUVEC, lymphoma, skeletal muscle, small intestine, stomach, Jurkat cells and uterus were screened using an RT-PCR generated product corresponding to SEQ ID NO:5. Edge (Edge Biosystems) unamplified cDNA libraries were prepared from stringently size-selected cDNA. cDNA insertion is performed utilizing a directional adaptor strategy which preserved representation. The vector used to prepare the library (pEAK8) contained the EBV latent origin of replication and an EBNA-1 transcription unit for plasmid replication in non-rodent cells and the SV40 origin for plasmid replication in cells expressing SV40 large T antigen. Insert expression was under the control of a modified version of the strong cell-type independent EF-1 á promoter. The cDNA libraries from these organs were made in a mammalian expression vector, pEAK8, Edge Biosystems Inc. (Gaithersburg, Md.). The library was screened by high throughput screening with an internal PCR probe (SEQ ID NO:5). The pEAK8 vector is a mammalian expression vector containing SV40 and EBV origin of replication, EF-1 alpha promoter, a poly linker site for cloning, a poly A and splice sites at the 3' end of the insert. The vector also contains Tk promoter driven puromycin gene for selection in mammalian cells, an EBNA-1 antigen tag and an ampicilin resistance gene for selection in bacteria. Forty-eight independent clones were isolated from this screening. All the clones were confirmed by PCR for the presence of internal sequence for the nucleic acid of SEQ ID NO:5. Plasmid DNAs were isolated from these 48 clones, PCR amplified with CCRG gene-specific primers, and restriction digested with EcoR1 and Not1 which cuts in the poly linker site of the pEAK8 vector, thus releasing the insert. The products were separated on 25 agarose gels and the products visualized by ethidium bromide staining. The products were confirmed to contain the nucleic acid of SEQ ID NO:5 by hybridization to an internal oligonucleotide probe.

Four independent clones strongly hybridizing to the probe were selected for sequencing. Sequencing was done using pEAK8 forward (5' GGA TCT TTG GTT CAT TCT CAA 3' SEQ ID NO: 11) and pEAK8 reverse (5' CTG GAT GCA GGC TAC TCT AG 3' SEQ ID NO:12). Both of these primers are present outside the cloning sites in the poly linker region of the pEAK8 vector. All the four clones contained additional sequences from the nucleic acid of SEQ ID NO:5. One of the clone, termed G6, contained a complete open reading frame with a signal peptide sequence. The g6 clone had an insert size of approximately 800 bp and detected a mRNA of about 750 bp in a Northern blot of colon tumor-derived RNA, but not in the normal colon mRNA. RT-PCR primers encompassing the entire G6 clone also detected a specific product in the colon tumor derived mRNAs, but not in the corresponding normal colon derived mRNAs. The G6 clone also contained a polyadenylation site and a poly A tail. The gene thus identified was termed CCRG for Colon Carcinoma Related Gene.

Example 3

Characterization of CCRG Protein

The CCRG gene has a signal peptide sequence M G P S S C L L L I L I P L L Q L I N P G S T Q C S L D S V (SEQ ID NO:13) upstream of the initiation Met codon. This consensus signal peptide sequence is found in secreted growth factors and cytokines. Using the SignaP prediction program at the Swiss Expasy site, the position for the signal peptidase cleavage of the CCRG gene is predicted to occur at GST-QC leaving a leader sequence of 7 amino acids before the Met codon of the mature CCRG protein. The PSORT program at the Expasy site which predicts the cell localization predicted that the CCRG gene is likely localized outside the cell. The mature protein has a theoretical MW of 8.62 kDa and pI of 8.05.

A CCRG gene, which was cloned in a Simian Virus 40 (SV40) expression vector was transfected into a recipient cells (e.g., COS-7 cells). The transfection resulted in expression of a CCRG protein in the supernatant of the media in which the transfected cells were cultured. When tested on colon carcinoma derived cells, the cell free supernatant stimulated DNA synthesis in the cells as monitored by $^3$H-thymidine incorporation. These results are consistent with the CCRG gene encoding a secreted product which has a growth stimulating property.

Nucleotide and amino acid homology searches at the NCBI revealed no significant homology to known proteins. Analysis of motifs and patterns at the ProCyte database of the Expasy site showed that the CCRG gene product likely encodes phosphorylation sites, myristylation sites, and glycosylation sites. In addition, a prokaryotic lipoprotein binding site and a prenylation site were identified as being encoded by the CCRG gene.

The C-terminus of the CCRG gene is cysteine rich with a motif 1CX11; 2CX8; 3CX1; 4CX3; 5CX10; 6CX1; 7CX1; 8CX9; 9C10C. This motif is also found in ultra high sulphur matrix protein in hair keratin, metallothionein and cation transporters. Three dimensional structure homology searches against the 3D database of PDB at the NCBI showed some structural homology to cartilage oligomeric matrix precursor and LDL-r related proteins. Secondary structure prediction program at the Expasy site predicted mostly a mixture of alpha helices, beta strands, and coils.

Example 4

Lack of CCRG Gene Expression in Non Colon-derived Solid Tumors

Figure 2:
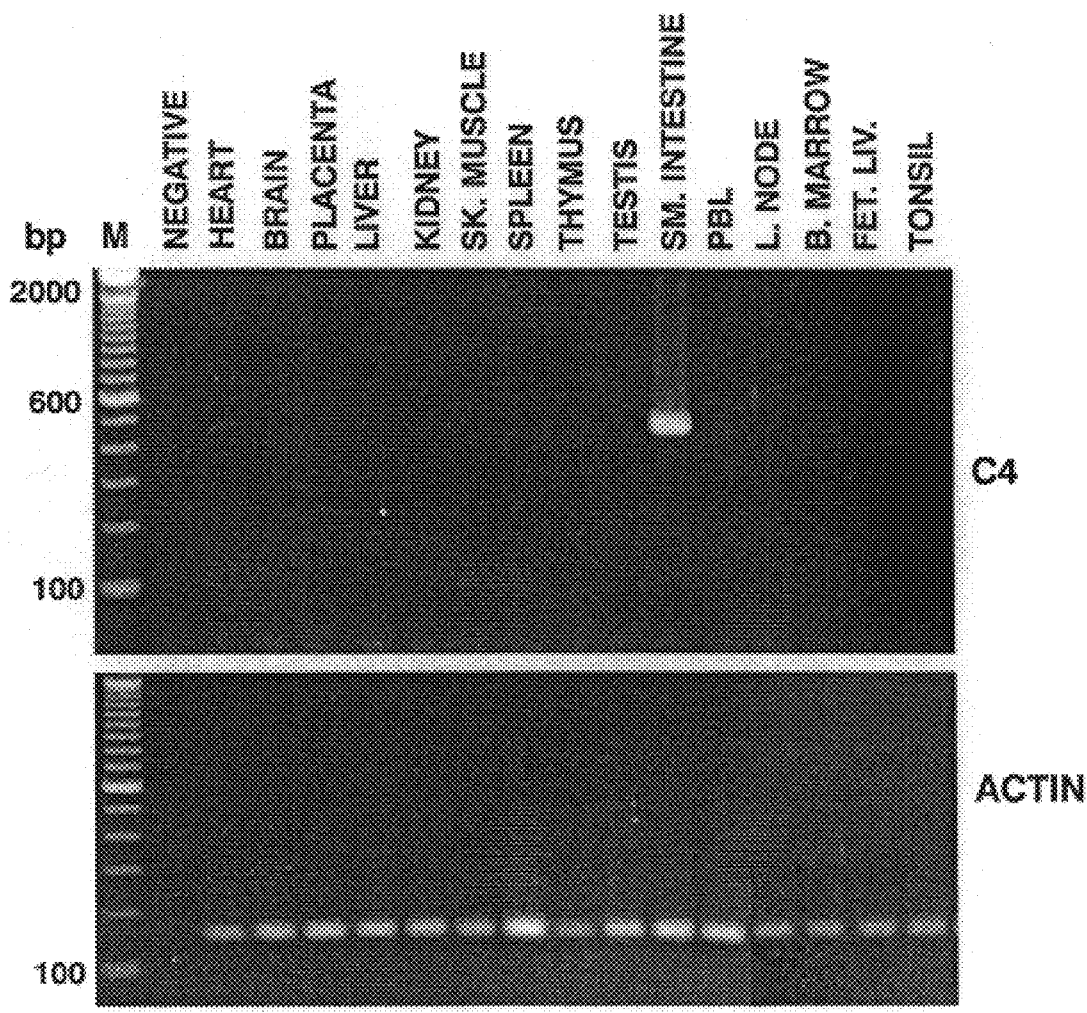
FIG. 2 is a photograph of an ethidium bromide-stained agarose gel after electrophoresis of cDNAs obtained from normal human tissues and analyzed by RT-PCR using SEQ ID NOs:2 and 3 as PCR primers. The actin gene was used as an internal control. M=100 bp ladder marker; Negative=template minus control.

In order to evaluate the specificity of expression of CCRG (C4) gene in colon tissues, a panel of cDNAs from diverse normal human tissues was obtained from Clontech Laboratories (Palo Alto, Calif.). These cDNAs were PCR amplified using the sense and the antis ense primers described respectively as SEQ ID NOs: 2 and 3. RT-PCR analysis of these cDNAs was performed as described herein. As shown in FIG. 2, the C4 (portion of the CCRG) gene was detected in small intestine, but not in heart, brain, placenta, liver, kidney, skeletal muscle, spleen, thymus, testis, peripheral blood lymphocytes, lymph nodes, bone marrow, fetal liver, tonsils, breast, colon, lung, ovary, pancreas and prostate. The samples were simultaneously analyzed for actin expression as an internal control.

Figure 3:
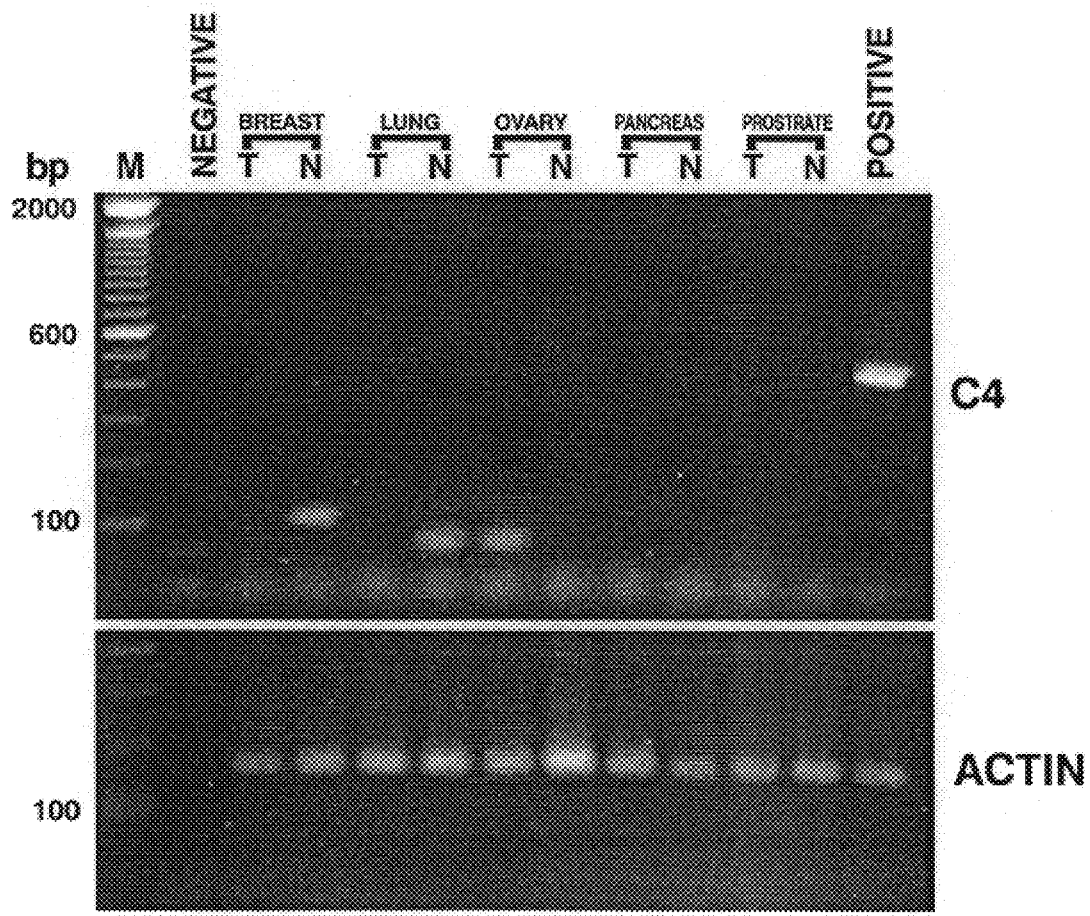
FIG. 3 is a photograph of an ethidium bromide-stained agarose gel after electrophoresis of cDNAs obtained from normal and tumor breast, lung, ovary, pancreas and prostate and analyzed by RT-PCR using SEQ ID NOs: 2 and 3 as PCR primers. The actin gene was used as an internal control. M=100 bp ladder; Negative=template minus control; Positive=colon tumor cDNA.

To further evaluate the specificity of CCRG expression to colon tumors, random primed cDNAs from five other solid tumors (breast, lung, ovary, prostate and pancreas) were generated using the RT method described herein. These cDNAs were PCR amplified using the sense and the antisense primers described as SEQ ID NOs: 2 and 3. As shown in FIG. 3, the amplified products were not detected in any of these tumor or normal tumor derived cDNAs. The samples were simultaneously analyzed for actin expression as an internal control.

Example 5

Colon Tumor Specific Upregulation of the CCRG Gene

Figure 4:
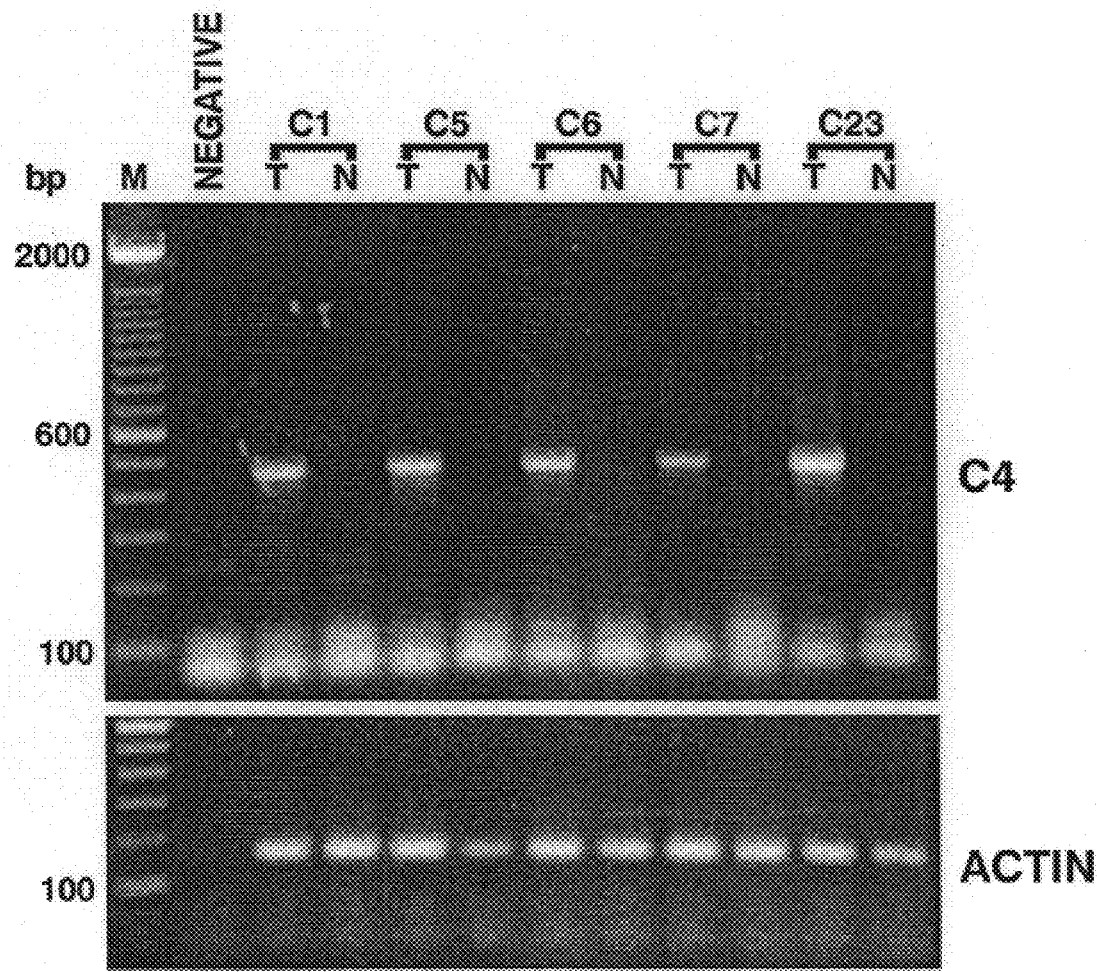
FIG. 4 is a photograph of an ethidium bromide-stained agarose gel after electrophoresis of cDNAs obtained from matched sets of tumor and normal colon samples from five different patients and analyzed by RT-PCR using SEQ ID NOs: 2 and 3 as PCR primers. The actin gene was used as an internal control. M=100 bp ladder; Negative=template minus control.

Further evidence that the CCRG gene expression is colon tumor specific was obtained using cDNAs derived from five different matched normal and tumor colon tissues. Random primed cDNAs were generated from the total RNAs from these tissues, and the cDNAs were PCR amplified using the sense and the antisense primers described in SEQ ID NOs: 2 and 3. As shown in FIG. 4, the CCRG (C4) gene was upregulated in each of the colon tumor tissues, but not in the matched normal tissues.

Example 6

Detection of the CCRG Gene by Hybridization Using an Oligonucleotide Probe

Figure 5:
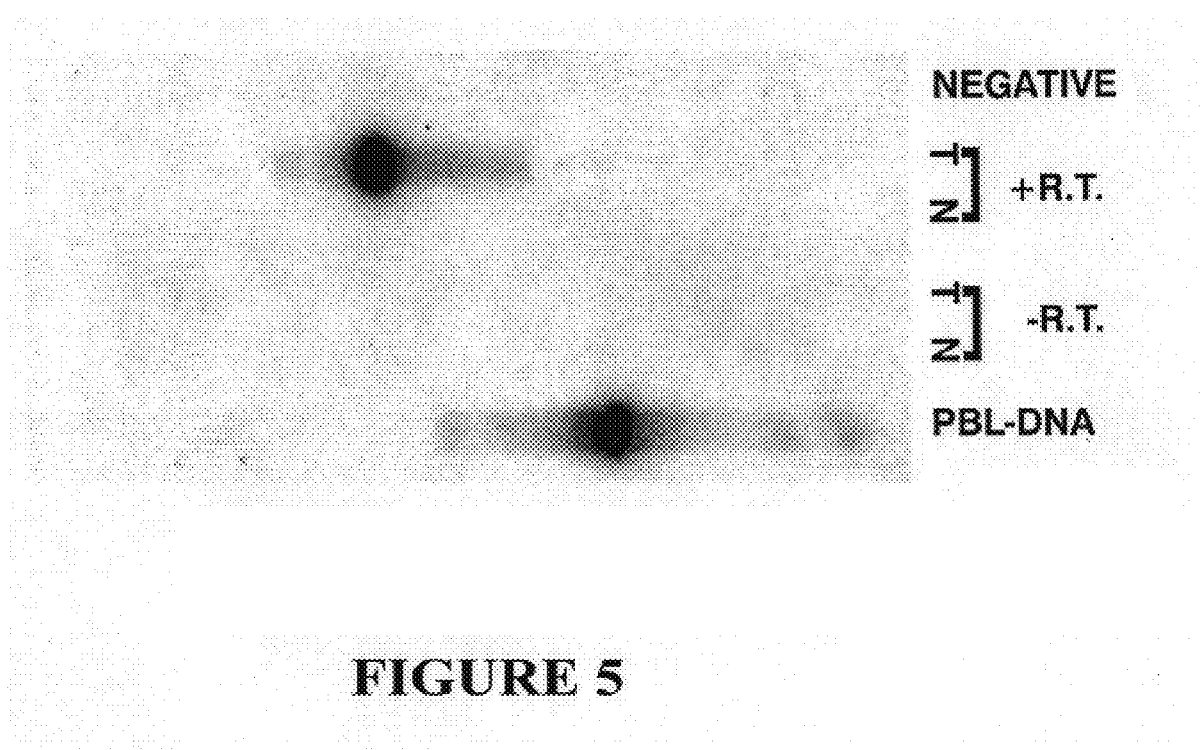
FIG. 5 is an autoradiograph of a blot of cDNAs obtained from a matched set of tumor and normal colon tissue samples. The cDNAs were PCR-amplified using SEQ ID NOs: 2 and 3 as the PCR primers. Amplification products were transferred to a nitrocellulose filter. The filter was hybridized to an end-labeled oligonucleotide (SEQ ID NO:4) probe and autoradiographed. +/−RT=cDNAs made with or without RT; Negative=template minus PCR control; T=colon tumor; N=normal colon; and PBL=genomic DNA from peripheral blood lymphocytes.

The CCRG gene was detected using of an oligonucleotide probe labeled with 32 P-labeled dNTP. An oligonucleotide corresponding to SEQ ID NO:4 was synthesized, and then end-labeled with gamma $^{32}$ P-labeled dATP using polynucleotide kinase. RT-PCR products were generated in the presence or absence of RT from a matched set of tumor and normal colon, transferred to a nitrocellulose membrane, and hybridized to the $^{32}$P-labeled oligonucleotide probe. As shown in FIG. 5, this probe hybridized to a 455 bp product in the tumor derived cDNA, but not in the normal tissue cDNA. The probe also detected a band in a genomic DNA (ca.1.5 kbp) sample obtained from peripheral blood lymphocytes.

Example 7

Diagnostic Process

Evaluation of CCRG gene expression is specifically envisioned as a method for diagnosing cancer. In this method, tissue to be examined is isolated from a patient (e.g., cells from polyps, adenomas carcinomas, etc. are obtained during routine colonoscopy). Total RNA obtained from these cells is then converted into cDNAs using either random primers or oligo dT to initiate the cDNA. The cDNAs obtained are PCR-amplified using the sense and the antisense primers described herein as SEQ ID NOs:2 and 3. The PCR-amplified products are then subjected to agarose gel electrophoresis, and the gel is stained to visualize the nucleic acid bands. The presence of a 455 bp product is indicative of potential cancer.

In addition, a method for diagnosing colon cancer using blood or blood-derived materials (e.g., serum) using the antibodies to the CCRG gene is an envisioned as the CCRG protein is predicted to be a secreted protein. CCRG protein levels above the baseline due to the production of the CCRG protein by intestine cells would be indicative of colon cancer in the patients. The levels of secreted CCRG protein in the serum/plasma can be measured by methods described elsewhere herein including, e.g., Enzyme Linked Immunosorbent Assay (ELISA) or Western blotting.

Example 8

Detection of the CCRG Gene by Hybridization

Using hybridization techniques, CCRG gene expression can be detected with the oligonucleotide probe described herein as SEQ ID NO:4. The oligonucleotide is labeled with radioactive or non-radioactive nucleotides, and the labeled probe is reacted with RNA from the sample being analyzed in the form of a Northern blot by transferring the products onto a filter (for example, nitrocellulose). This method can also be performed in the form of Southern blot of RT-PCR reaction products made from the genomic DNA contained in a sample being analyzed. Following hybridization to the oligonucleotide probe, the filter is washed, exposed to X-ray film, and auto-radiographed. Bands that hybridized to the probe can be identified from the autoradiogram. The oligonucleotide probe can also be used for in situ hybridization reactions to directly detect CCRG gene expression in tissues.

Example 9

Detection of Cancer Cells

A method for detecting cancer cells (e.g., metastatic cancer cells) is specifically envisioned. The method involves obtaining a tissue sample from a test subject (e.g., a cancer patient), optionally isolating nucleic acid (e.g., by PCR amplification) or protein from the sample, probing the sample or isolated nucleic acid/protein with a molecule that specifically binds to CCRG genomic DNA, mRNA or cDNA, or the corresponding polypeptide product (e.g., CCRG protein). For example, in one variation of this method, total RNA is isolated from cancer cells obtained from fecal or peripheral blood samples. The RNA is then analyzed for the presence of CCRG mRNA by RT-PCR using the oligonucleotides of SEQ ID NOs:2 and 3 as primers. As another example, CCRG gene expression can be detected in the cells of these samples by in situ hybridization using SEQ ID NO:4 as a oligonucleotide probe. As still another example, antibodies specific for CCRG protein can be used to probe cells samples directly (e.g., using conventional immunofluorescence, histochemical staining techniques) or can be used to detect CCRG protein by immunoprecipitation and electrophoresis, or by Western blotting.

Example 10

CCRG as a Therapeutic Target

Inhibition of CCRG gene expression can be accomplished using an antisense nucleic acid. For example, a suitable length (e.g., 18–25 bases) of an antisense nucleic acid that specifically hybridizes to the 5' prime-coding region of the CCRG gene is synthesized, and then introduced into target tissues or cells (e.g., by electroporation or delivery via a vector) or liposomes. The target tissues or cells are then placed under conditions that allow the anti-sense nucleic acid to hybridize to the mRNAs transcribed from the CCRG gene. This hybridization prevents translation and thereby to selectively inhibits expression of CCRG protein. See, e.g., Narayanan, R. In Vivo, 8: 787–794, 1994. As another example, the foregoing antisense nucleic acid can also generated as a stable recombinant construct that can be delivered in vivo for gene therapy. See, e.g., Higgins et al., Proc Nat'l Acad Sci USA 90: 9901–9905, 1993.

In one variation of this example, the antisense nucleic acid is the oligonucleotide shown as SEQ ID NO:8 (i.e., 5' TCC TTG ATC TTC TTA TCC ATA ACG 3'). This oligonucleotide can be substituted with various components at the nucleic acid backbone. Tumor-bearing patients can be treated with suitable formulations of this antisense oligonucleotide as described, e.g., Narayanan R and Akhtar S., Curr Opin Oncol 8: 509–515, 1996; Higgins et al., Proc Nat'l Acad Sci USA 90: 9901–9905, 1993; and Narayanan R, J. Nat'l. Cancer Inst. 89: 107–109, 1997. The antisense oligonucleotide can be used alone or in combination with conventional chemotherapy or radiotherapy protocols.

Example 11

CCRG as a Drug Discovery Target

A method of discovering drugs that selectively modulate CCRG protein function is envisioned. In this method, an expression vector incorporating a nucleic acid encoding a CCRG protein is introduced into and expressed in a host cell under conditions that cause the CCRG protein to be produced in the cell. The CCRG protein produced in this manner is then purified so that it can be used in an in vitro high throughput assay to screen for compounds that bind to it. Those compounds that bind the CCRG protein can be isolated and further characterized. For example, such compounds could be tested for the ability to inhibit the growth of CCRG expressing tumor-derived cell lines in growth inhibition assays.

As another method for discovering drugs, a substance to be screened can be added to a culture containing a cell expressing CCRG to see if the substance modulates CCRG expression. In an alternative method, cell lines transfected with recombinant constructs containing a reporter gene (e.g., those that encode chloramphenicol acetyltransferase, luciferase, beta-galactosidase, etc.) operably linked to the CCRG promoter can be used to identify substances that inhibit expression of the CCRG gene. For example, compounds that selectively inhibit expression of the reporter would be identified as a CCRG selective inhibitor.

As CCRG is selectively expressed in colon tumors; but not in a variety of other tumors, compounds can be screened for the ability to selectively inhibit growth of CCRG-expressing tumors. Compounds identified in this manner can be further evaluated for CCRG-specific inhibition using the CCRG promoter-reporter gene constructs described above.

Example 12

CCRG Receptor as a Drug Target

Since at least one form of CCRG protein is a secreted molecule, it is possible that there exists a cellular receptor to which CCRG protein binds. Such a receptor can be identified by those skilled in art, for example by labeling a CCRG protein with a detectable label (e.g., radioactive iodine), and then using the labeled CCRG protein to identify the receptor molecules present in the colon cancer cell membranes. The identified receptor protein can be sequenced and, using such sequence, the full length clone of such a receptor can be obtained. The cloned receptor can be used in screening assays to detect specific agonists/antagonists and the lead drugs can be tested in colon cancer cells to determine whether the compound can inhibit the growth of the colon cancers.

Example 13

Antibody Detection of CCRG

Tumor selective expression of a CCRG gene product can be detected by measuring expression of CCRG protein using such techniques as immunohistochemistry or immunofluorescence. As an example of the latter technique, paraffin-fixed sections of colon tumor and corresponding normal tissues are analyzed using antibodies specific for CCRG protein. Immunohistochemical detection of CCRG protein is performed using the techniques described in Scheurle et al., Anticancer. Res. 20:2091–2096, 2000. In brief, the sections are deparaffinized in a xylene bath two times for five minutes, and then rehydrated through graded alcohols to distilled water. Slides are incubated with the primary anti-CCRG antibody. Bound primary antibody is detected by staining the sections with an enzyme labeled secondary antibody that specifically binds the primary antibody. The slides are developed using a chromagen compatible with the enzyme label. The sections are counterstained with hematoxylin, dehydrated in ethanol, and mounted in Permount (Fisher Scientific). Using this method, CCRG protein expression should be detectable in colon tumors but not in normal tissues. In view of the predicted secreted nature of the CCRG protein, use of anti-CCRG antibodies in Western blots or ELISAs is therefore specifically envisioned in methods for detecting CCRG protein in tissue samples as a diagnostic or prognostic assay for CCRG-associated malignancies.

Other Embodiments

This description has been by way of example of how the compositions and methods of invention can be made and carried out. Those of ordinary skill in the art will recognize that various details may be modified in arriving at the other detailed embodiments, and that many of these embodiments will come within the scope of the invention.

Therefore, to apprise the public of the scope of the invention and the embodiments covered by the invention, the following claims are made.

What is claimed is:

1. A method for detecting a colon cancer cell in a biological sample comprising the steps of:
   (a) providing the biological sample; and
   (b) detecting the presence in the biological sample of a CCRG polypeptide having the amino acid sequence of SEQ ID NO:7, wherein an increase in the level of the CCRG polypeptide in the biological sample indicates that the biological sample as compared to the level in a normal control sample contains a colon cancer cell.

2. The method of claim 1, wherein the step (b) of detecting the presence of the CCRG polypeptide in a biological sample comprises:
   contacting the biological sample with a probe that binds to the CCRG polypeptide; and
   detecting binding of the probe to the biological sample.

3. The method of claim 1, wherein the step (b) of detecting the presence of the CCRG polypeptide in a biological sample comprises:
   isolating polypeptides from the biological sample;
   separating the polypeptides from each other;
   contacting the separated polypeptides with a molecule that binds to the CCRG polypeptide; and
   detecting binding of the molecule to the CCRG polypeptide.

4. The method of claim 1, wherein the biological sample is a cell derived from a colon.

5. The method of claim 4, wherein said colon is a human colon.

6. The method of claim 1, wherein the biological sample is feces or urine.

7. The method of claim 1, wherein the biological sample is selected from the group consisting of blood, plasma, and serum.

8. The method of claim 2, wherein the probe is an antibody.

9. The method of claim 8, wherein the antibody is a monoclonal antibody.

10. The method of claim 9, wherein the monoclonal antibody is labeled with a detectable label.

11. The method of claim 10, wherein the detectable label is selected from the group consisting of a radioisotope, a fluorescent compound, a bioluminescent compound, a chemiluminescent compound, biotin, colloidal gold, a magnetic particle, and an enzyme.

12. The method of claim 8, wherein the antibody is a polyclonal antibody.

13. The method of claim 12, wherein the polyclonal antibody is labeled with a detectable label.

14. The method of claim 13, wherein the detectable label is selected from the group consisting of a radioisotope, a fluorescent compound, a bioluminescent compound, a chemiluminescent compound, biotin, colloidal gold, a magnetic particle, and an enzyme.

15. The method of claim 1, wherein the step (b) of detecting the CCRG polypeptide comprises contacting the biological sample with a first antibody that specifically binds to the CCRG polypeptide.

16. The method of claim 15, wherein the polypeptide is immobilized on a substrate.

17. The method of claim 16, further comprising contacting the substrate with a second antibody that is labeled with a detectable label, wherein said second antibody specifically binds to said first antibody.

* * * * *

SEQUENCE LISTING

<160> NUMBER OF SEQ ID NOS: 13

<210> SEQ ID NO 1
<211> LENGTH: 576
<212> TYPE: DNA
<213> ORGANISM: homo sapiens

<400> SEQUENCE: 1

```
tgaggtacaa agtttgtctt tattacccaa gaatcaggaa tggaacaaat gaagtgggac      60
gtttgagtta gatttcttgg ttgggaccct ggtttcatta ctgtcatggt cacaaactga     120
gttctcagcc tcctccctgt caggtcaggt ggcagcagcg ggcagtggtc cagtccacca     180
cactgcactg gcagtggcag gtggtttcca gctgaacatc ccacgaacca cagccatagc     240
cacaagcaca gccagtgaca gccatcccag cagggcagtg aggacggtct gccttggctt     300
ttgacactag cacacgagag cttcttgctt ataggagagg gactgtactc tagactgttg     360
agaacatcct tgatcttctt atccataacg gagtctaagg aacactgagt actcccgggg     420
ttgatcagct ggagaagggg gattaggatg agaaggaggc aagaggacgg ccccatcctg     480
tacagagtca gtgtcctggg gctgggggaa agatggaaag agcttagatc tctgagccct     540
gggtggtggt gaggaaagaa gacacgtggc tcgtgc                               576
```

<210> SEQ ID NO 2
<211> LENGTH: 22
<212> TYPE: DNA
<213> ORGANISM: homo sapiens

<400> SEQUENCE: 2

```
gagttctcag cctcctccct gt                                               22
```

<210> SEQ ID NO 3
<211> LENGTH: 21
<212> TYPE: DNA
<213> ORGANISM: homo sapiens

<400> SEQUENCE: 3

```
cgagccacgt gtcttctttc c                                                21
```

<210> SEQ ID NO 4
<211> LENGTH: 20
<212> TYPE: DNA
<213> ORGANISM: homo sapiens

<400> SEQUENCE: 4
acaagcacag ccagtgacag    20

<210> SEQ ID NO 5
<211> LENGTH: 744
<212> TYPE: DNA
<213> ORGANISM: homo sapiens

<400> SEQUENCE: 5

```
gcctcagaca gtggttcaaa gttttttct tccatttcag gtgtcgtgaa aagcttgaat      60
tcggcgcgcc agatatcaca cgtgccaagg ggctggctca aataaatctg ttcttcagca    120
accctacctg cttctccaaa ctgcctaaag agatccagta ctgatgacgc tgttcttcca    180
tctttactcc ctggaaacta accacgttgt cttctttcct tcaccaccac ccaggagctc    240
agcgatctaa gctgctttcc atcttttctc ccagcccag acactgact ctgtacagga     300
tgggccgtc ctcttgcctc cttctcatcc taatcccct tctccagctg atcaacccgg      360
ggagtactca gtgttcctta gactccgtta tggataagaa gatcaaggat gttctcaaca    420
gtctagagta cagtccctct cctataagca agaagctctc gtgtgctagt gtcaaaagcc    480
aaggcagacc gtcctcctgc cctgctggga tggctgtcac tggctgtgct tgtggctatg    540
gctgtggttc gtgggatgtt cagctggaaa ccacctgcca ctgccagtgc agtgtggtgg    600
actgaccac tgcccgctgc tgccacctga cctgacaggg aggaggctga gaactcagtt     660
ttgtgaccat gacagtaatg aaaccagggt cccaaccaag aaatctaact caaacgtccc    720
actttatttg ttvvattcat ttgt                                           744
```

<210> SEQ ID NO 6
<211> LENGTH: 887
<212> TYPE: DNA
<213> ORGANISM: homo sapiens

<400> SEQUENCE: 6

```
gcctcagaca gtggttcaaa gttttttct tcctttcagg tgtcgtgaaa agcttgaatt     60
cggcgcgcca gatatcacac gtgccaaggg gctggctcaa ataaatctgt tcttcagcaa    120
ccctacctgc ttctccaaaa ctgcctaaag agatccagta ctgatgacgc tgttcttcca    180
tctttactcc ctggaaacta accacgttgt cttctttcct tcaccaccac ccaggagctc    240
agagagatct aagctgcttt ccatcttttc tcccagcccc aggacactga ctctgtacag    300
gatggggccg tcctcttgcc tcttctcat cctaatcccc cttctccagc tgatcaaccc    360
ggggagtact cagtgttcct tagactccgt tatggataag aagatcaagg atgttctcaa    420
cagtctagag tacagtccct ctcctataag caagaagctc tcgtgtgcta gtgtcaaaag    480
ccaaggcaga ccgtcctcct gccctgctgg gatggctgtc actgctgtgc ttgtggctat    540
ggctgtggtt cgtgggatgt tcagctggaa accaccctgc cactgccagt gcagtgtggt    600
ggactggacc actgcccgac tgctgccacc tgacctgaca gggaggaggc tgagactcag    660
ttttgtgacc atgacagtaa tgaaaccagg gtcccaacca agaaatctaa ctcaaacgtc    720
cacttcattt gttccattcc tgattcttgg gtaataaaga caaactttgt acctctcaaa    780
aaaaaaaaa aaaagtatt tcattacctc tttctccgca cctggcctgc agccggccgc     840
```
aggtaagcca gcccaggcct cgccctccag ctaaggcggg acagggc        887

<210> SEQ ID NO 7
<211> LENGTH: 111
<212> TYPE: PRT
<213> ORGANISM: homo sapiens

<400> SEQUENCE: 7

Met Gly Pro Ser Ser Cys Leu Leu Ile Leu Ile Pro Leu Leu Gln
1               5                   10                  15

Leu Ile Asn Pro Gly Ser Thr Gln Cys Ser Leu Asp Ser Val Met Asp
                20                  25                  30

Lys Lys Ile Lys Asp Val Leu Asn Ser Leu Glu Tyr Ser Pro Ser Pro
            35                  40                  45

Ile Ser Lys Lys Leu Ser Cys Ala Ser Val Lys Ser Gln Gly Arg Pro
        50                  55                  60

Ser Ser Cys Pro Ala Gly Met Ala Val Thr Gly Cys Ala Cys Gly Tyr
65                  70                  75                  80

Gly Cys Gly Ser Trp Asp Val Gln Leu Glu Thr Thr Cys His Cys Gln
                85                  90                  95

Cys Ser Val Val Asp Trp Thr Thr Ala Arg Cys Cys His Leu Thr
            100                 105                 110

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: Antisense oligonucleotide
<220> FEATURE:
<221> NAME/KEY: misc_feature
<223> OTHER INFORMATION: Antisense Oligonucleotide

<400> SEQUENCE: 8
tccttgatct tcttatccat aacg        24

<210> SEQ ID NO 9
<211> LENGTH: 22
<212> TYPE: DNA
<213> ORGANISM: Homo sapiens

<400> SEQUENCE: 9
ggccgtcctc ttgcctcctt ct        22

<210> SEQ ID NO 10
<211> LENGTH: 24
<212> TYPE: DNA
<213> ORGANISM: Homo sapiens

<400> SEQUENCE: 10
ggtttccagc tgaacatccc acga        24

<210> SEQ ID NO 11
<211> LENGTH: 21
<212> TYPE: DNA
<213> ORGANISM: ARTIFICIAL SEQUENCE
<220> FEATURE:
<223> OTHER INFORMATION: pEAK vector primer

<400> SEQUENCE: 11
ggatctttgg ttcattctca a        21

```
<210> SEQ ID NO 12
<211> LENGTH: 20
<212> TYPE: DNA
<213> ORGANISM: ARTIFICIAL SEQUENCE
<220> FEATURE:
<223> OTHER INFORMATION: pEAK vector primer

<400> SEQUENCE: 12
ctggatgcag gctactctag                                            20

<210> SEQ ID NO 13
<211> LENGTH: 30
<212> TYPE: PRT
<213> ORGANISM: Homo sapiens

<400> SEQUENCE: 13

Met Gly Pro Ser Ser Cys Leu Leu Ile Leu Ile Pro Leu Leu Gln
1               5                   10                  15

Leu Ile Asn Pro Gly Ser Thr Gln Cys Ser Leu Asp Ser Val
            20                  25                  30
```